United States Patent [19]
Ross et al.

[11] 4,118,866
[45] Oct. 10, 1978

[54] DENTAL HANDPIECE CONTROL APPARATUS

[75] Inventors: Robert G. Ross, E. Northport, N.Y.; Mark M. McCracken, Richardson, Tex.

[73] Assignee: Parkell Products, Inc., Farmingdale, N.Y.

[21] Appl. No.: 714,943

[22] Filed: Aug. 16, 1976

[51] Int. Cl.² ............................................. A61C 19/02
[52] U.S. Cl. .................................... 32/22; 32/DIG. 3
[58] Field of Search .................. 32/22, DIG. 3, 26, 27

[56] References Cited

U.S. PATENT DOCUMENTS

| | | | |
|---|---|---|---|
| 3,673,709 | 7/1972 | Page | 32/22 |
| 3,886,660 | 6/1975 | Thornton, Jr. et al. | 32/22 |

FOREIGN PATENT DOCUMENTS

| | | | |
|---|---|---|---|
| 2,339,824 | 2/1975 | Fed. Rep. of Germany | 32/22 |
| 1,450,122 | 9/1976 | United Kingdom | 32/22 |

*Primary Examiner*—Russell R. Kinsey
*Assistant Examiner*—Robert P. Swiatek
*Attorney, Agent, or Firm*—Wolder, Gross & Yavner

[57] ABSTRACT

A dental air-water handpiece control system for operating a plurality of handpieces and an air-water syringe including a plurality of control pedals equal in number to the number of handpieces and each having a needle valve responding to the distance the pedal moves when operated. Replaceable control modules are also included, with each module servicing a single handpiece and having a main control valve regulating air-water flow to the handpiece it services. Diaphragms control the operation of the main control valves and a laminated base plate defines channels for air and water flow through the unit.

A water pressure regulator and an air gauge are also provided in the system.

8 Claims, 14 Drawing Figures

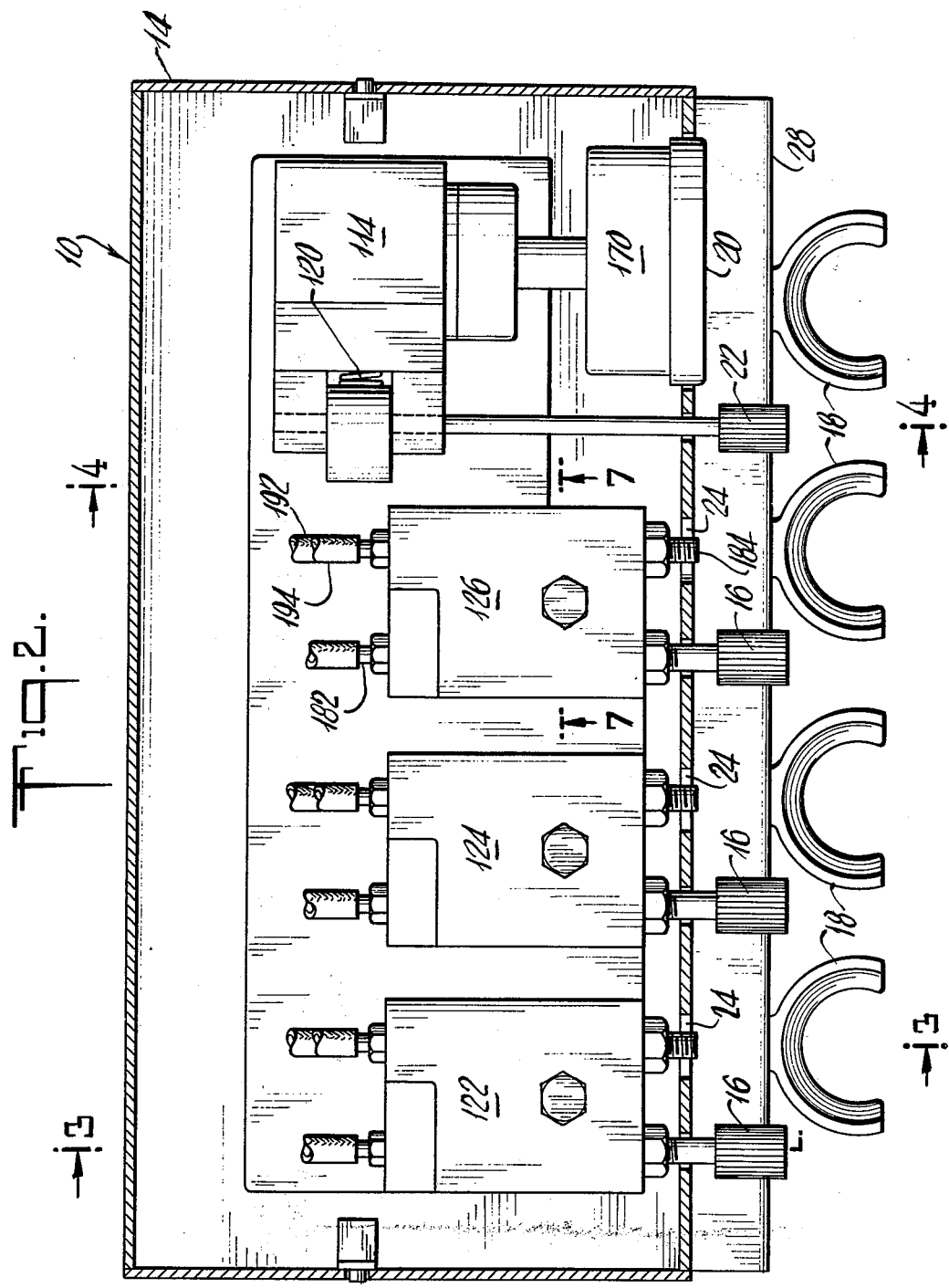

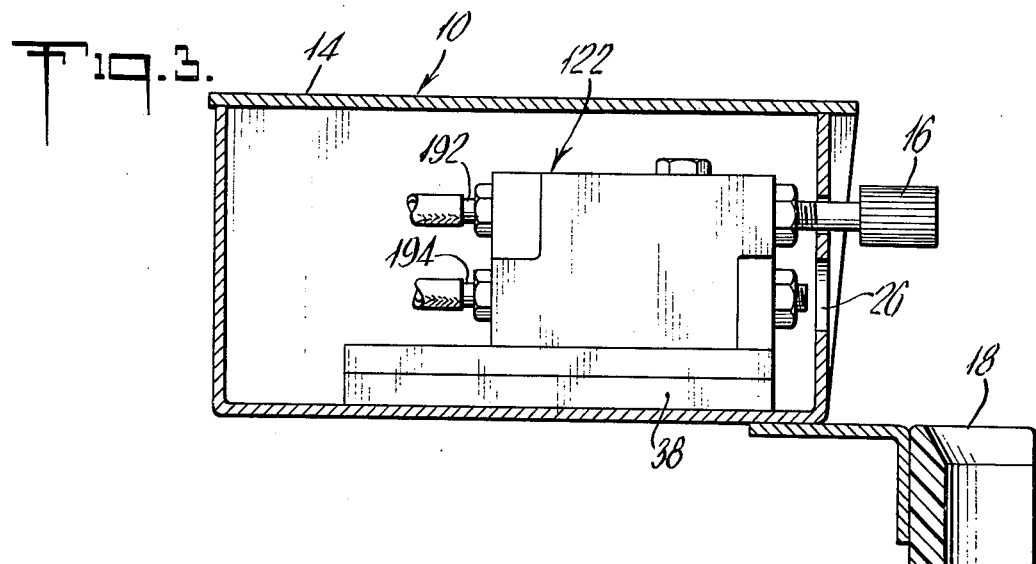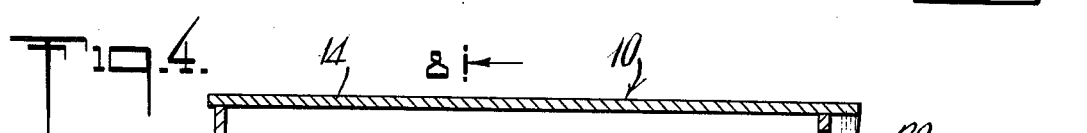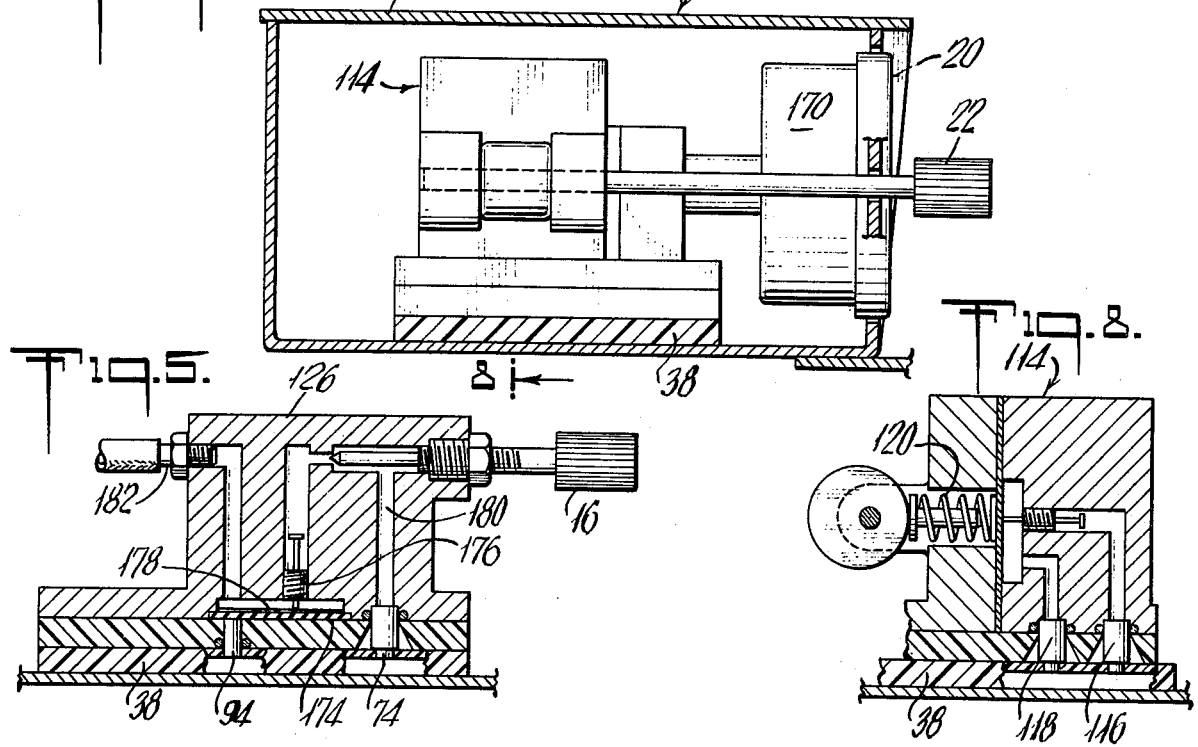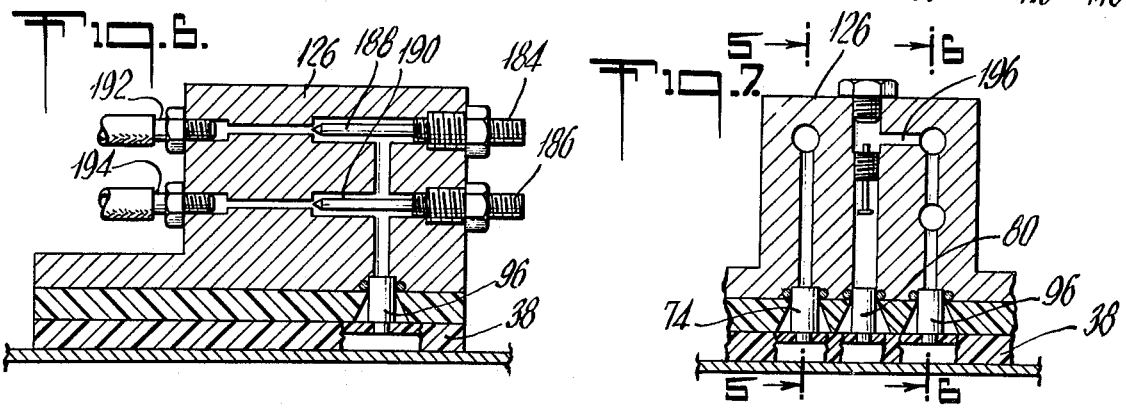

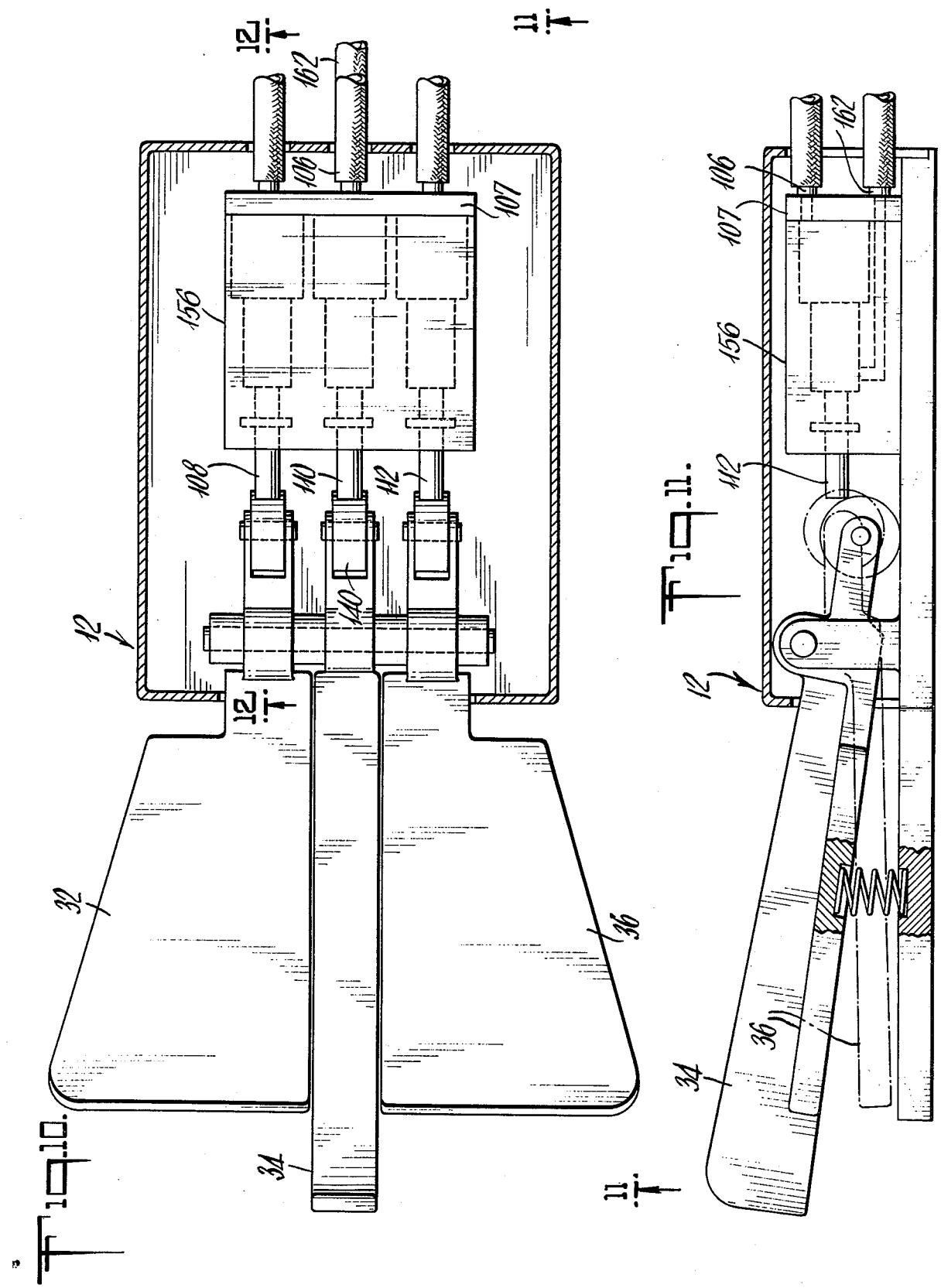

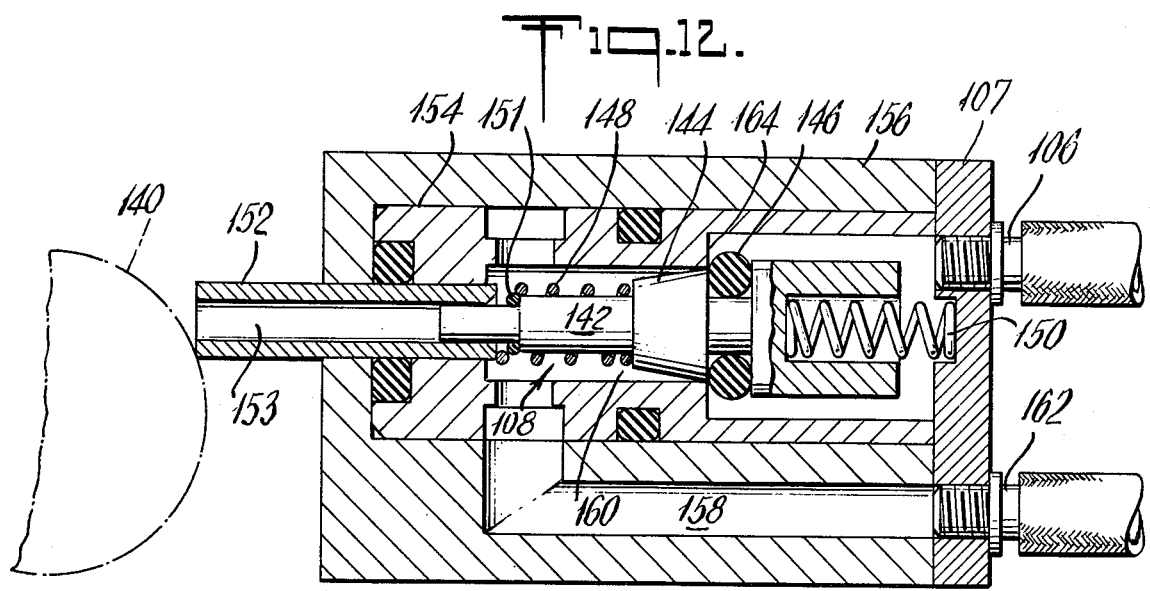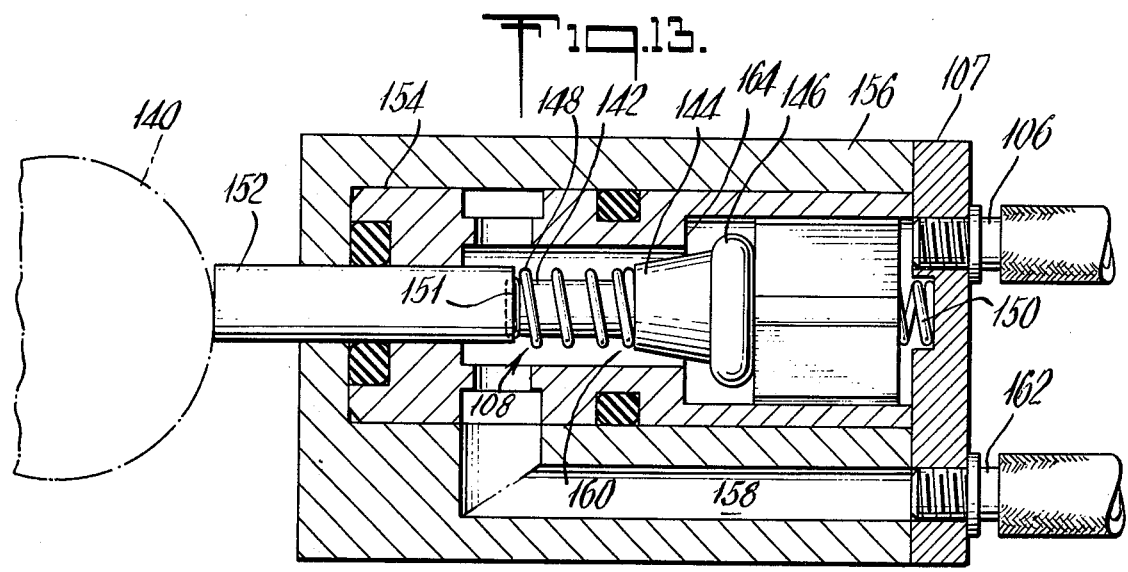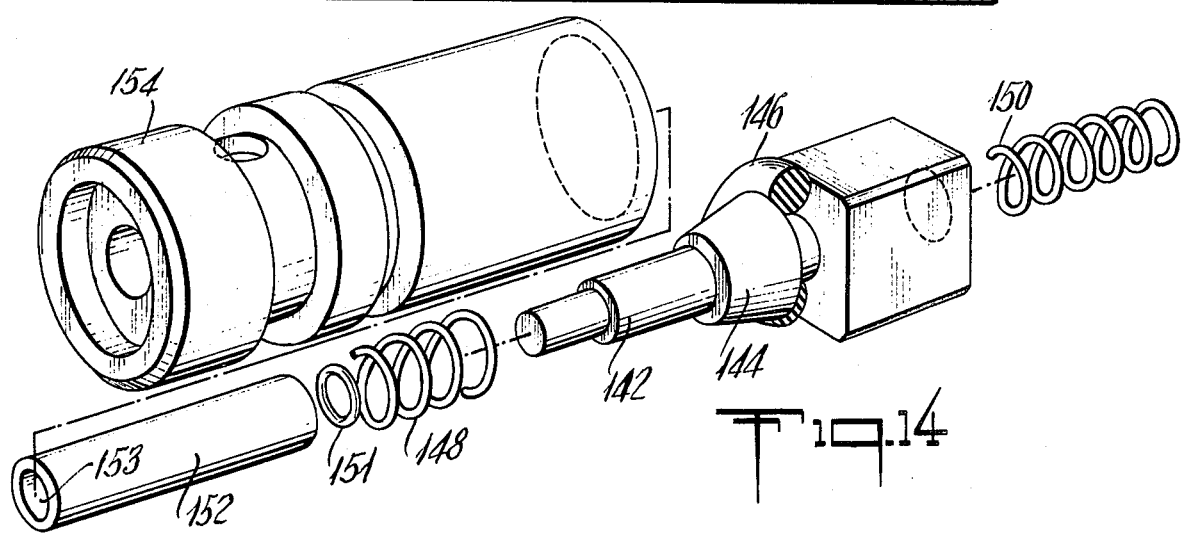

DENTAL HANDPIECE CONTROL APPARATUS

This invention relates primarily to dental handpiece control systems and more particularly to such systems including pedal control and primarily mechanical, as distinguished from electrical or primarily pneumatic, operation.

The present state of the art with respect to dental handpiece control systems involves usually a single pedal air control and inter-dependent water control apparatus. With reference to the pedal control, a single malfunction within this unit would eliminate the capability for any operation by the apparatus, since usually more than one handpiece is serviced by the apparatus and it is not uncommon to experience breakdown in one of the valves or elsewhere in the control apparatus. Furthermore, a great many hoses and conduits are usually an important part of such present day apparatus. Still further, a breakdown, as mentioned previously, usually involves servicing the unit without the concurrent capability to make use of the unit during its repair.

The state of the art with respect to this field is also encumbered by a multitude of valves, lockout mechanisms and electrical and pneumatic devices, all of which are subject to frequent breakdown and attendant loss of useable operating time.

The present day apparatus as heretofore described has also proven to be inconvenient, cumbersome and otherwise unsatisfactory in terms of its operation and utility.

Accordingly, a primary object of the present invention is to provide a convenient, reliable and structurally simple apparatus for controlling dental handpieces.

Another object of the present invention is to provide such apparatus without the encumbrance of unnecessary valves, lockout mechanisms and electrical or primarily pneumatic devices usually present in dental handpiece control apparatus.

Still another object of the present invention is to provide dental handpiece control apparatus in which most conduits and hoses are replaced by aesthetically acceptable mechanical units which are hidden from view of either the operator or patient.

Another object of the present invention is to provide dental handpiece apparatus wherein the main control devices are in the form of replaceable modules enabling easy repair and replacement in the event of breakdown without affecting other such control modules in the system.

Further, it is an object of the present invention to provide dental handpiece control apparatus in which a plurality of foot control pedals are provided in accordance with the number of handpieces to be operated, in order to avoid system shutdown when a single pedal control malfunctions.

These and other objects of the present invention are provided in a dental handpiece control system which features a plurality of handpieces and an air-water syringe to be controlled in terms of its air and water supply, a pedal control unit including a plurality of pedals equal in number to the plurality of handpieces, with each including a needle valve responding to the distance of motion of the pedal connected to that valve. A control module is also provided for each handpiece, with each module being separately and conveniently replaceable without affecting the operation of other parts of the system or other modules. A base plate defining air and water flow channels to each module is provided to replace a multitude of tubes and other conduits presently encumbering state of the art systems. An air-water syringe receives air from one of the channels of the base plate and water from another of the channels. A water pressure regulator receives water from the base plate and regulates the pressure and flow of the water to the control modules. Within the modules, main control valves control water flow to the handpieces. Air flow is controlled by a needle valve at each control pedal and such valves enable air flow from the base plate to one of the pedals and back to the base plate for distribution to the main control valves of the control modules. Associated with each main control valve is a diaphragm which responds to air flow from the base plate to thereby control water flow through the main control valves. The distributed air flow in each of the modules is metered off for handpiece cooling and handpiece drive. Furthermore, air is also metered off in the modules for flow through the base plate and to enable this pressure to be registered on an air gauge (common to all modules) to provide a reading for air flow in accordance with control by needle valves in each control module. Release of the control pedals in turn releases air to the atmosphere and a spring is provided for each of the main control valves for returning the diaphragm to its normal position and to prevent water drip at the handpieces. The water pressure regulator includes means for reducing water pressure and terminating water flow to the handpieces and all in all, a complete control system is presented in a simple, reliable and efficient structure which includes many advantages over the state of the art.

The above description, as well as further objects, features and advantages of the present invention will be more fully appreciated by reference to the following detailed description of the preferred, but nontheless illustrative, embodiment, when taken in conjunction with the accompanying drawings, wherein:

FIG. 3 is a side sectional view of the dental unit of FIG. 2, taken along the line 3—3 thereof and showing particularly a control module and handpiece mount;

FIG. 4 is a side sectional view of the master water switch for the apparatus taken along the line 4—4 of FIG. 2;

FIG. 5 is a side sectional view through a control module, taken along the line 5—5 of FIG. 7 and showing particularly the main control valve and diaphragm of the module;

FIG. 6 is another side sectional view through a control module at line 6—6 of FIG. 7 and showing particularly the air inlet thereof and the means by which air is metered off for various uses in the system;

FIG. 7 is a front sectional view taken along the line 7—7 of FIG. 2 and showing particularly the air inlet for the module and means by which air is metered off for various uses;

FIG. 8 is a front sectional view taken along the line 8—8 of FIG. 4 and showing particularly the master water switch and controls for the present invention;

FIG. 9 is a top view of the base plate of the dental unit shown in FIG. 1 and illustrates particularly the air and water flow channels defined in the base plate for use in the system of the present invention.

FIG. 10 is a partially sectioned top view taken along the line 10—10 of FIG. 1 and showing particularly the pedal control unit of the present invention with a pedal control being provided for each handpiece of the system;

FIG. 11 is a side sectional view taken along the line 11—11 of FIG. 10 and showing particularly the pedal operating mechanism;

FIG. 12 is an enlarged side sectional view of the control mechanism for one of the pedals and taken along the line 12—12 of FIG. 10, with the control mechanism being shown with its parts in a position before depression of the pedal;

FIG. 13 is a representation similar to that shown in FIG. 12 but with the mechanism having its parts in position when the pedal is depressed; and FIG. 14 is an exploded isometric view of parts of the operating mechanism for the pedal operating controls shown in FIGS. 12 and 13.

Figure 1:
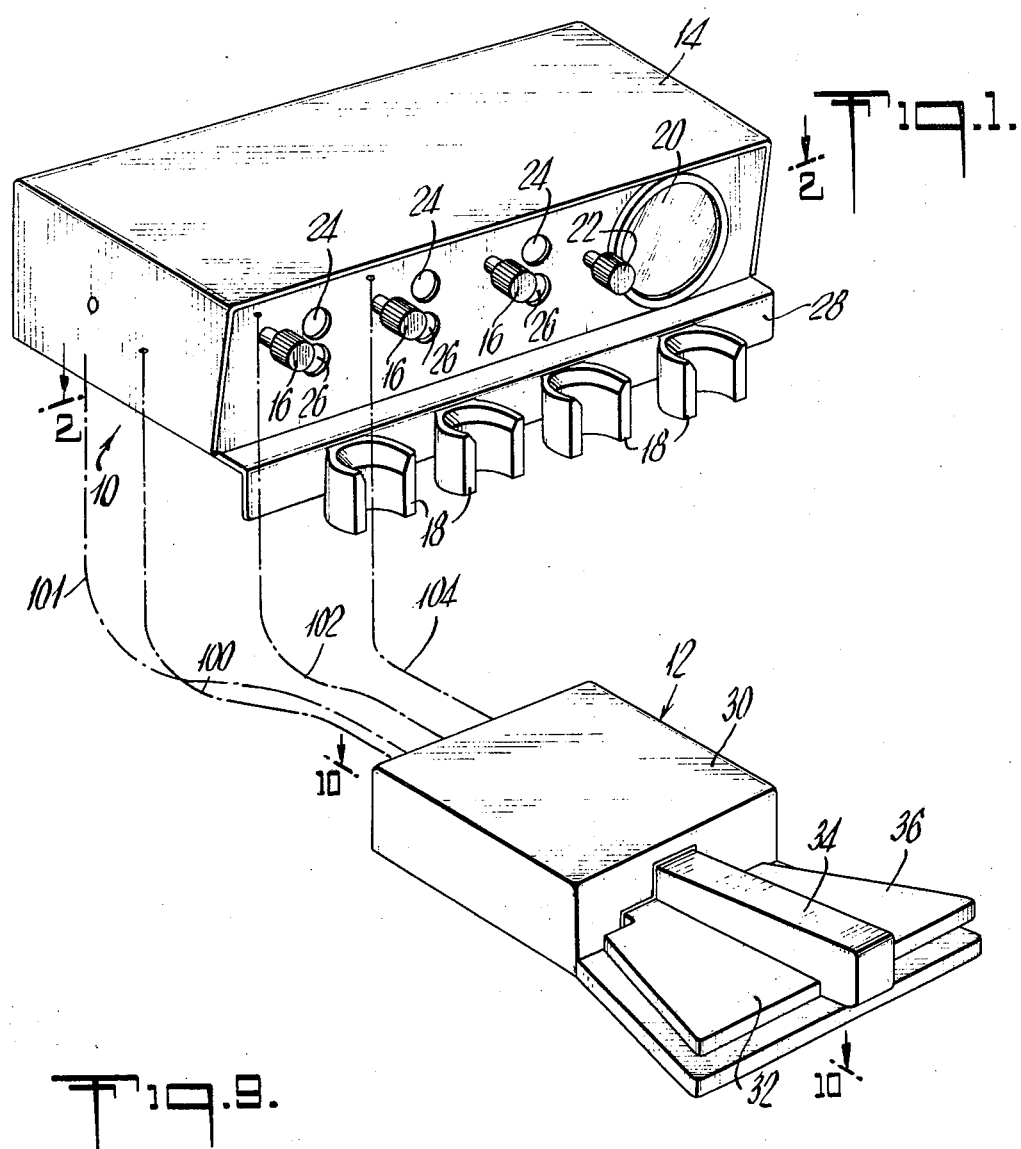
FIG. 1 is an isometric representation of a dental handpiece control system in accordance with the present invention showing particularly the exterior of the pedal control unit and the exterior of the dental unit which includes the base plate, the control modules, the air gauge display, control knobs and means for mounting handpieces and other apparatus.

FIG. 1 represents an exterior view of the apparatus of the present invention. Specifically, dental unit 10 is a major sub-section of the apparatus and pedal control unit 12, the other main sub-section. Dental unit 10 includes a main housing 14 defining apertures through which control knobs 16 for adjusting the volume of water to the handpieces (not shown) are accessible. Brackets 18 are for mounting the handpieces and/or other such dental apparatus, such as an air-water syringe. Furthermore, window 20 is for displaying a representation of air pressure by means of an air pressure gauge, whose function will be described hereinafter. Also, knob 22 is for a master water switch control which will also be described in this specification.

Dental unit housing 14 also defines upper openings 24 through which protrudes means by which air for driving turbines of the handpieces may be controlled. Lower openings 26 are defined to provide access means for controlling the flow of air to provide atomization of the water flowing to the handpieces. Flange 28 is for mounting brackets 18 and with the other external features of dental unit 10 provides a compact and convenient main sub-section for the apparatus of the present invention.

Pedal control unit 12 includes a control housing 30, protruding from which are three control pedals 32, 34, 36. Of course, pedals can be replaced by other forms of valves or a distributing valve can be used to supply air to a number of tubes for activating a plurality of modules.

Within dental unit 10 and attached to the bottom plate thereof is a laminated base plate 38 (FIG. 9) which defines a plurality of channels 40, 42, 44, 46, 48, 50, 52 and a plurality of apertures 54–98 whose function is primarily to guide the flow of air and water to and from the various parts of the apparatus. More specifically, base plate 38 is laminated to provide an ease of construction of the channels and holes and to enable the ease of manufacture of variations in the designs of such channels and holes to accommodate other and additional uses for the apparatus.

Referring primarily to FIGS. 1 and 9, the apparatus operates in connection with a supply of air (not shown) with the air being introduced to the apparatus at aperture 54, after which such air flows along channel 52 and out of aperture 56 to enter pedal control unit by means of a hose 100 (shown in ghost lines in FIG. 1 for clarity of presentation). Air enters pedal control unit 12 through inlet 106 (FIG. 12) and the use of such air is then under the control of foot pedal 32. Specifically, needle valves 108, 110, 112 (FIG. 10) stop the air flow until actuation of pedals 32, 34, 36 respectively, occurs.

At this point it might be mentioned that aperture 58 is an air outlet from channel 52 for the purpose of flow to an air-syringe connection (not shown).

Water is introduced to the apparatus from any suitable source (not shown) to base plate 38 at aperture 62. Such water flow is channeled along channel 42 to aperture 60 and then to a syringe connection (not shown). Water also flows along channel 42 from aperture 62 to aperture 64 and then to the master water switch 114 (FIGS. 4 and 8), which functions as a water pressure regulator for the system. Water pressure regulator 114 accepts such flow at its inlet 116 for return to base plate 38 by means of water pressure regulator outlet 118 (FIG. 8). The water pressure regulator 114 operates by building up water pressure at the outlet to equalize the pressure with spring 120. Flow of a pressure reduced water at a time then occurs back to base plate 38. From water pressure regulator 114, water flows back to the base plate and enters at aperture 66 for distribution through apertures 68, 72, 74 to control modules 122, 124, 126. respectively.

Such modules are depicted more specifically in FIGS. 2, 3, 5–7 and the function of such modules will be described with reference to both air and water flow after a brief discussion of air control by pedal control unit 12.

Referring to FIGS. 10–14, the pedal control unit 12 is shown with its inlets 106. The action of needle valves 108, 110, 112 commences by depressing control pedals 32, 34, 36, respectively, and for the purposes of clarity, a sigle pedal operation will be disclosed with respect to control pedal 32. As control pedal 32 is depressed, the distance it is depressed will enable the action of cam 140 (FIGS. 12 and 13). The cam is shown in FIG. 12 in the position it would assume when control pedal 32 is at rest (not depressed). Depression of control pedal 32 moves cam 140 to the position in FIG. 13. Needle valve unit 108 in FIGS. 12–14, includes a stepped shaft 142 affixed to a tapered collar 144, whose widest point abuts O-ring 146. Front and rear of stepped shaft 142 are surrounded by springs 148, 150 and front spring 148 is driven by driving tube 152 which abuts cam 140. The needle valve unit 108 is inserted to sleeve 154 (FIG. 14) and sleeve 154 is, in turn, inserted to needle valve housing 156. Needle valve housing 156 and sleeve 154 combine to form channels 158 (outlet channel) and 160 (valve channel).

Specifically, as cam 140 moves driving tube 152 rightwardly (in the orientation of FIGS. 12–14), by action of pedal 32 being depressed, tube 152 closes the valve exhaust by means of O-ring 151. Tube 152 also moves spring 148 which in turn moves tapered collar 144 also in the rightward direction. Tapering of collar 144 has a metering effect — the motion to the right opens the flow channel more for increasing flow. As may be seen most clearly from FIG. 13 such motion of tapered collar 144 will enable air flow to move through valve channel 160 to outlet channel 158 and then to outlet 162.

Upon release of pedal 32, cam 140 will again assume the position shown in FIG. 12 and the action of spring 150 will return tapered collar 144 to the position shown in FIG. 12 with O-ring 146 abutting shoulder 164 to stop air flow coming from inlet 106 and spring 148 moves tube 152 away (leftwardly) to break the seal of O-ring 151. Air is exhausted through exhaust channel 153 within tube 152.

Figure 2:
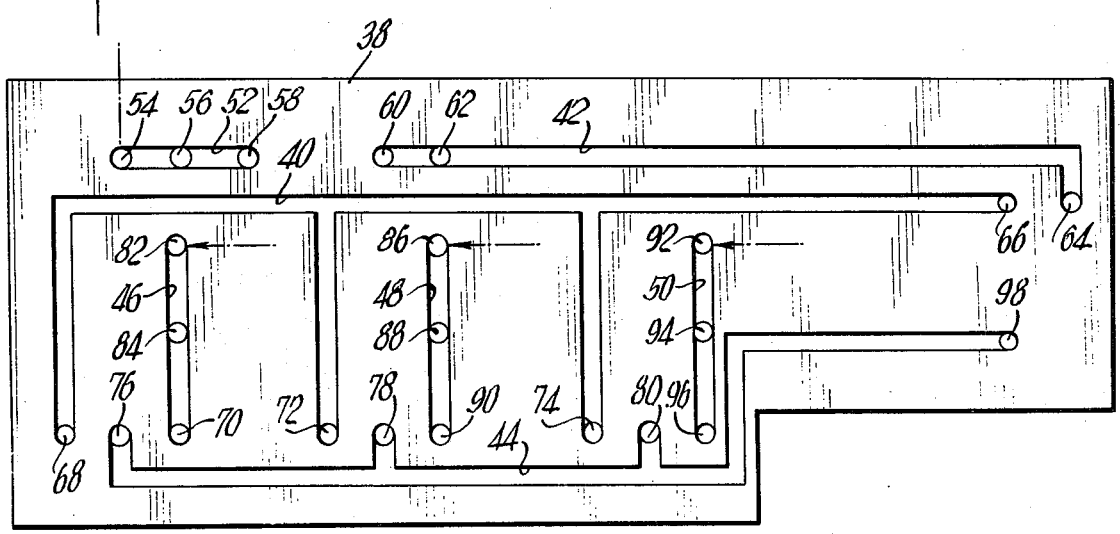
FIG. 2 is a top, partial sectional view of the handpiece unit taken along the line 2—2 of FIG. 1 and showing particularly the control modules of the present invention and the air gauge thereof.

When needle valve 108 enables air flow through outlet 162, such air flow will traverse tubing 101 (FIG. 1) to base plate 38. Actually, one inlet for air flow (tube 100) serves all pedal control units by means of manifold 107. Each pedal control unit has an outlet (tubes 101, 102, 104). Such air flow from the pedal control units enters base plate 38 at aperture 92, from which it traverses channel 50 to apertures 94, 96 and into module 126. More specifically, apertures 94 and 96 are inlets of module 126 (FIGS. 5, 6, 7). Furthermore, aperture 80 is an air outlet of module 126 for air gauge 170 (FIG. 2).

Thus, both water flow (aperture 74) and air flow (apertures 94, 96) have reached module 126 and the use of such air and water will now be discussed with reference to FIGS. 5–7 particularly.

Air entering at the module inlet (aperture 94) will move diaphragm 174 upwardly in the orientation of the drawing. Such motion by diaphragm 174 will open main water control valve 176 by pressure from plate 178 to enable the flow of water from the water inlet (aperture 74) through channel 180, past valve 176 and through outlet 182 to the handpiece (not shown) associated with module 126. Of course, such water flow presumes proper positioning of control knob 16 (FIGS. 1 and 5) associated with module 126. As explained previously, such control knobs 16 are for the purpose of adjusting the volume of the water flowing to the handpieces through each module.

Referring to FIG. 6, it may be seen that adjustment screws 184, 186 (which in FIG. 1 would be accessible through upper and lower openings 24, 26) are for the purpose of adjusting valves 188, 190 (needle valves) which, respectively, meter off air flowing through aperture 96 to be used from outlet 192 as driving air for turbines of the handpieces and through outlet 194 as air to atomize the water flow at the handpieces.

Air exiting module 126 (FIG. 7) flows through check valve 196 through aperture 80 along channel 44 of base plate 38 to aperture 98 and air guage 170. Check valve 196 is used to prevent air flow to the other handpiece modules.

Furthermore, a spring is provided in association with each diaphragm 174 to return the diaphragm to its rest position when the pedals 32, 34, 36 are released. Also the action of such springs prevent water drip at the handpieces.

What is claimed is:

1. A dental air-water handpiece control system for use with a source of water and a source of air and for operating a plurality of handpieces and an air-water syringe, comprising a variable speed foot control including separate pedals for each handpiece, a control module for each handpiece, a laminated base plate defining channels for enabling water and air flow, an air-water syringe for receiving air from one of said channels and water from one of said channels, a water pressure regulator for receiving water from said base plate and distributing water-pressure-regulated water to said control modules, a main water control valve in each of said control modules for controlling water flow therethrough, a needle valve operated by each of said pedals for enabling air flow to said base plate for distribution to one of said main water control valves, a plurality of diaphragms for controlling said main control valves to enable water flow therethrough in response to air flow distributed by said needle valve and means for enabling water flow from said main control valve to said handpiece and means in each of said modules for enabling metering of said distributed air flow for handpiece cooling and handpiece drive.

2. The invention according to claim 1 wherein said main water control valves in said modules are start-stop valves.

3. The invention according to claim 1 wherein one of said needle valves releases air to the atmosphere when its pedal is released.

4. The invention according to claim 1 wherein said water pressure regulator includes means for terminating water flow to said handpieces.

5. A dental air-water handpiece control system for use with a source of water and a source of air and for operating a plurality of handpieces and an air-water syringe, comprising a pedal control unit including a plurality of pedals, each for separately controlling operation of a particular handpiece, a plurality of separable and replaceable control modules, each for controlling air and water flow for a particular handpiece and a laminated base plate defining channels for enabling water and air flow, said base plate receiving air from said source of air and for distributing air to said pedal control unit for control by said pedals and said base plate receiving water from said source of water and for distributing said water through said modules in response to action of said pedals, all adapted and arranged to operate one handpiece by use of one module and one pedal, without regard to operability of other modules and pedals.

6. The invention according to claim 5 wherein a water regulator for the system is provided to receive water from said base plate, regulate the pressure of said water and return regulated water to said base plate for distribution through said modules in response to action of said pedals.

7. The invention according to claim 5 wherein said pedal control unit includes a valve for controlling air flow comprising an inlet means, an outlet, an exhaust, a flow control for controlling flow volume, means for moving said flow control to an open position and means for returning said flow control to a closed position, said flow control including a tapered member and said exhaust including a seal which opens after motion of said tapered member to its closed position.

8. The invention according to claim 5 wherein said modules each include valves for metering off air flow received from a pedal of said pedal control unit to drive one of said handpieces and to atomize water thereat.

* * * * *